United States Patent [19]

Bey et al.

[11] 4,277,395

[45] Jul. 7, 1981

[54] NOVEL ENZYME INHIBITORS

[75] Inventors: Philippe Bey, Strasbourg, France; Brian W. Metcalf, Mason; Jeffrey S. Wiseman, Loveland, both of Ohio

[73] Assignee: Richardson-Merrell Inc., Wilton, Conn.

[21] Appl. No.: 160,111

[22] Filed: Jun. 16, 1980

[51] Int. Cl.³ .................. C07C 103/52; C07D 207/24
[52] U.S. Cl. .......................... 260/112.5 R; 260/326.2; 260/326.4; 260/326.47; 260/326.48; 560/24; 560/32; 560/159; 560/169; 564/136; 564/152; 564/153; 564/159
[58] Field of Search ............ 260/112.5 R, 326.4, 260/326.2, 326.48, 326.47; 564/136, 152, 153, 159; 560/32, 24, 159, 169

[56] References Cited

U.S. PATENT DOCUMENTS 4,176,116  11/1979  Hassall et al. ............ 260/112.5 R

*Primary Examiner*—Delbert R. Phillips
*Attorney, Agent, or Firm*—John J. Kolano; Raymond A. McDonald; Salvatore R. Conte

[57] ABSTRACT

Compounds of the following general formula are irreversible inhibitors of pancreatic elastase:

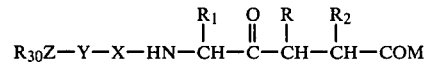

wherein M is hydroxy, lower alkoxy, benzyloxy or $-NY_1Y_2$ wherein each of $R_4$ and $R_5$ is hydrogen or lower alkyl; R is $CF_3$, $CHF_2$ or $CH_2F$; $R_1$ is straight or branched lower alkyl; $R_2$ is defined the same as $R_1$ or is benzyl; $R_{30}$ is CHO, carbobenzoxy, tert-butoxycarbonyl, benzoyl or lower alkanoyl; X is pro, ala or leu and Y and Z together form a single bond; or Y-X is ala-pro, ala-ala or ala-leu and Z forms a single bond; and Z-Y-X is ala-ala-pro, ala-ala-ala or pro-ala-leu.

6 Claims, No Drawings

NOVEL ENZYME INHIBITORS

BACKGROUND OF THE INVENTION

This invention relates to novel chemical compounds active as inhibitors of elastase, rendering said compounds useful in the treatment of emphysema, pancreatitis and rheumatoid arthritis.

Elastase has been identified as playing a significant role in the etiology of a number of biological activities including emphysema of lung tissue, pancreatitis and arthritis. See, for example, Joseph Bieth et al., Biochemical Medicine 11, 350–357 (1974); Conrad P. Dorn et al., J. of Medicinal Chemistry 20, 1464–1468 (1977); and Cedric H. Hassall, Bioorganic Chemistry 8, 299–309 (1979). Compounds that are known to be inhibitors of elastase have been identified as having utility in the treatment of emphysema, rheumatoid arthritis and pancreatitis. See, for example, U.S. Pat. Nos. 4,029,772, 4,153,688 and 4,176,116.

The present invention provides a new series of fluoromethylated elastase inhibitors and chemical intermediates useful in the preparation of said inhibitors.

SUMMARY OF INVENTION

The compounds of the following general Formula XVI and pharmaceutically acceptable salts thereof are useful pharmacologic agents.

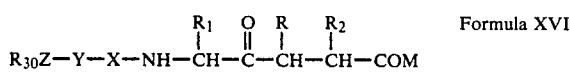
Formula XVI

In the above general Formula XVI, R is $CF_3$, $CHF_2$ or $CH_2F$; $R_1$ is a straight or branched lower alkyl group having from 1 to 4 carbon atoms, for example, methyl, ethyl, n-propyl, isopropyl, n-butyl, tert-butyl and the like; $R_2$ is defined the same as $R_1$ or is benzyl; $R_{30}$ is CHO, carbobenzoxy, tert-butoxycarbonyl, benzoyl or a lower alkanoyl group having from 2 to 5 carbon atoms, for example, acetyl, n-propionyl, isopropionyl, n-butyryl and the like; X is pro, ala or leu and Y and Z together form a single bond; or Y-X is ala-pro, ala-ala or ala-leu and Z is a single bond; or Z-Y-X is ala-ala-pro, ala-ala-ala or pro-ala-leu; and M is hydroxy, or a straight or branched lower alkoxy group having from 1 to 4 carbon atoms, such as methoxy, ethoxy, isopropoxy, n-propoxy, n-butoxy and the like or benzyloxy or $NY_1Y_2$ wherein each of $Y_1$ and $Y_2$ is hydrogen or a lower alkyl group having from 1 to 4 carbon atoms, for example, methyl, ethyl or n-propyl and $Y_1$ and $Y_2$ can be the same or different.

Pharmaceutically acceptable salts of the compounds of Formula XVI are also included in the scope of the present invention. The compounds of Formula XVI and pharmaceutically acceptable salts thereof are useful in the treatment of lung emphysema, pancreatitis and arthritis.

Also described in the present application are the compounds of the following general Formula I, said compounds being chemical intermediates for the preparation of the compounds of Formula XVI.

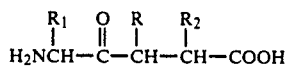
Formula I

In the above general Formula I the symbols R, $R_1$ and $R_2$ have the same meanings as set forth in Formula XVI.

DETAILED DESCRIPTION OF INVENTION

Referring to general Formula XVI and in particular to the symbols Z-Y-X, pro means the residue of the amino acid proline; ala, the residue of alanine; and leu, the residue of leucine.

Hence, X means

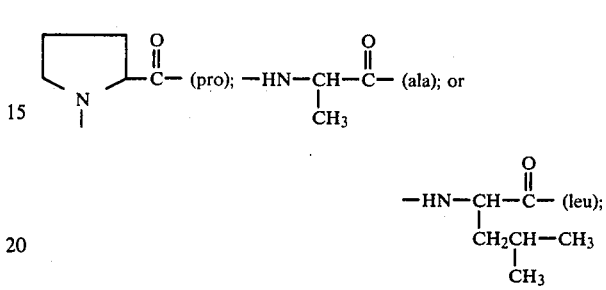

and Y and Z together form a single bond linking the nitrogen atom of the amino acid residue to $R_{30}$.

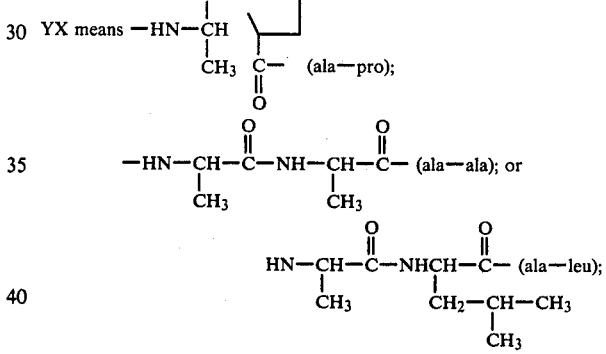

and Z forms a bond attaching the nitrogen atom of the Y amino acid residue to $R_{30}$.

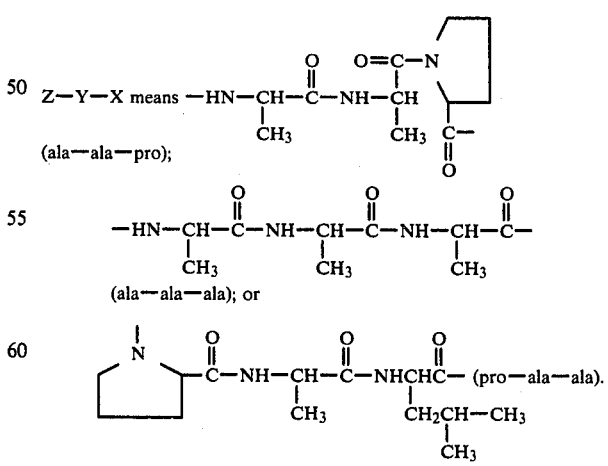

In the foregoing, the amino acid functions pro, leu and ala, which make up X, Y and Z, are in the naturally-occurring L-configuration.

Illustrative examples of pharmaceutically acceptable base salts of the compounds of general Formula XVI include non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Illustrative compounds of the above general Formula XVI are the following:
3-(formylprolylalanyl)-4-fluoro-2-methylbutyric acid,
3-(carbobenzoxyalanylalanyl)-4,4-difluoro-2-methylbutyric acid ethyl ester,
3-(acetylleucylalanyl)-4-fluoro-2-benzylbutyric acid benzyl ester,
3-(acetylalanylprolylanyl)-4-fluoro-2-ethylbutyramide,
3-(benzoylalanylprolylalanyl)-4-fluoro-2-ethylbutyramide,
3-(formylalanylalanylalanyl)-4,4-difluorobutyric acid tert-butyl ester, and
N,N-dimethyl-3-(acetylprolylalanylleucyl)-4-fluoro-2-benzylbutyramide.

Illustrative compounds of the above general Formula I are the following:
3-alanyl-4-fluoro-2-methylbutyric acid,
3-alanyl-4,4-difluoro-2-benzylbutyric acid,
3-leucyl-4,4,4-trifluoro-2-methylbutyric acid, and
3-alanyl-4-fluoro-2-ethylbutyric acid.

The compounds of Formula XVI and pharmaceutically acceptable salts thereof are inhibitors of elastase as demonstrated by their ability to inhibit irreversibly porcine pancreatic elastase. The assay for elastase inhibitory activity is generally that described by Cedric H. Hassall et al., Bioorganic Chemistry 8, 199–309 (1979). As a result of their enzyme inhibitory activity the compounds of Formula XVI and pharmaceutically acceptable salts thereof are useful in the treatment of emphysema of the lungs, pancreatitis and arthritis.

In practicing the present invention the compounds of Formula XVI and pharmaceutically acceptable base salts thereof (hereinafter sometimes referred to as "compounds of this invention" or "subject compounds") may be used alone or admixed with pharmaceutically acceptable carrier. Said compounds or salts can be administered to the patient being treated either orally or parenterally, for example, subcutaneously, intravenously or intraperitoneally. Also, said compounds or salts can be administered by intranasal instillation or by application to mucous membranes such as those of the nose, throat or bronchial tubes, for example, in droplet form or as an aerosol spray containing small particles of the compound or salt in a spray solution or dry powder form.

The compounds of this invention can be expediently administered in a dosage range of from about 0.1 to about 500 mg per day. It will, of course, be appreciated that this dosage range is given by way of example only and that it can be varied upwards or downwards depending on factors, such as the particular subject compound to be administered, the particular condition to be treated and the individual requirements of the patient as determined by the attending physician. For example, when administered for the treatment of emphysema of the lungs, an effective amount of subject compound may vary from about 0.1 to about 150 mg/kg, and preferably about 10–100 mg/kg. of body weight of the patient needing same, per day; when administered for the treatment of pancreatitis, an effective amount may vary from about 10 to about 200 mg/kg, and preferably about 10–100 mg/kg, of body weight of the patient needing same per day; and when administered for the treatment of arthritis; an effective amount may vary from about 10 to about 500 mg/kg, and preferably about 10–250 mg/kg, of body weight of the patient needing same per day. As used herein, the term "patient" is taken to mean warm blooded animals, such as mammals, for example, domestic, laboratory and food-supplying animals, e.g., cats, dogs, rats, mice, guinea pigs, sheep, horses, cattle, cows and the like, and humans.

The solid unit dosage forms can be of the conventional pharmaceutical type. Thus, the solid form can be a capsule which can be of the ordinary gelatin type containing a novel compound of this invention and a pharmaceutically acceptable carrier, for example, lubricant and inert fillers such as lactose, sucrose and corn starch. In another embodiment, the subject compounds are tableted with conventional tablet bases such as lactose, sucrose or corn starch in combination with binders such as acacia, corn starch or gelatin, disintegrating agents such as corn starch, potato starch or alginic acid, and a lubricant such as stearic acid, or magnesium stearate.

For parenteral administration, the compounds of this invention may be administered as injectable dosages of a solution or suspension of the compound in a physiologically acceptable diluent or carrier which can be a sterile liquid such as water and oils with or without the addition of a surfactant and other pharmaceutically acceptable adjuvants. Illustrative of oils which can be employed in these parenteral preparations are those of petroleum, animal, vegetable or synthetic origin, for example, peanut oil, soybean oil and mineral oil.

In general, water, saline, aqueous dextrose and related sugar solutions, alcohols such as ethanol and glycols such as propylene glycol or polyethylene glycol, including mixtures thereof, are preferred liquid carriers, particularly for injectable solutions.

The subject compounds can also be administered in the form of a depot injection or implant preparation which may be formulated according to conventional pharmaceutical techniques as to permit a sustained release of the active ingredient. The subject compound can be compressed into pellets or small cylinders and implanted subcutaneously or intramuscularly as depot injections or implants. Implants may employ inert materials such as biodegradable polymers or synthetic silicones.

For use as aerosols the compounds of this invention in solution or suspension may be packaged in a pressurized aerosol container together with suitable propellants, for example, hydrocarbon propellants, such as propane, butane or isobutane, or carbon dioxide or nitrogen or other environmentally acceptable propellants with the usual adjuvants such as cosolvents, and wetting agents, as may be necessary or desirable. The compounds may also be administered in a non-pressurized form such as in a nebulizer or atomizer.

An illustrative composition for hard gelatin capsules is as follows:

| (a) | 3-(acetylalanylprolylalanyl)-4-fluoro-2-methylbutyric acid | 20 mg |

| | | |
|---|---|---|
| (b) | talc | 5 mg |
| (c) | lactose | 90 mg |

The formulation is prepared by passing the dry powders of (a) and (b) through a fine mesh screen and mixing them well. The powder is then filled into hard gelatin capsules at a net fill of 115 mg per capsule.

An illustrative composition for tablets in as follows:

| | | |
|---|---|---|
| (a) | 3-(acetylprolylalanyl)-4,4-difluoro-2-benzylbutyric acid | 20 mg |
| (b) | starch | 43 mg |
| (c) | lactose | 45 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

An illustrative composition for an injectable suspension is the following 1 ml ampul for an intramuscular injection:

| | | Weight percent |
|---|---|---|
| (a) | 3-(formylalanylleucylalanyl)-4-fluoro-2-methylbutyric acid methyl ester | 1.0 |
| (b) | polyvinylpyrrolidone | 0.5 |
| (c) | lecithin | 0.25 |
| (d) | water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

The compounds of Formula XVI wherein M is a straight or branched alkoxy group having from 1 to 4 carbon atoms or is benzyloxy are prepared by converting the acid function of an appropriate compound of Formula I to the corresponding lower alkly or benzyl ester and reacting in equimolar amounts said ester with a compound of the formula $$R_{30}Z-Y-X-OH \qquad \text{Formula XVII}$$

wherein $R_{30}$, Z, Y and X have the meanings defined in Formula XVI. The reaction is carried out in dichloromethane or ether containing a base, such as, a tertiary amine and a suitable coupling reagent such as N-ethoxycarbonyl-2-ethoxy-1,2-dihydroquinoline (EEDQ), dicyclohexylcarbodiimide (DCC) or bis-trimethylsilylcarbodiimide (TMSN=C=N-TMS). The reaction is permitted to proceed for about 5 to 24 hours at a temperature of about 0° to 25° C.

The compounds of Formula XVI wherein M is hydroxy are prepared by treating the corresponding derivative wherein M is tert-butoxy with trifluoroacetic acid at about 0° to 25° C. for about 1 to 2 hours and then concentrating the reaction mixture to afford the free acid.

The compounds of Formula XVI wherein M is $NY_1Y_2$ are prepared by treating the corresponding derivative wherein M is hydroxy with a secondary amine of the formula $HNY_1Y_2$ wherein $Y_1$ and $Y_2$ have the meanings defined in Formula XVI. The reaction is carried out in methylene chloride or ether in the presence of a suitable coupling reagent such as EEDQ, DCC or TMSN=C=N-TMS at a temperature of about 0° C. to 25° C. for about 1 to 24 hours.

The compounds of Formula I are converted to the corresponding straight or branched lower alkyl $C_{1-4}$ ester (excepting tert-butyl) or the benzyl ester by allowing the appropriate compound of Formula I to stand at 25° C. for about 12 to 24 hours in the appropriate lower alcohol, such as, for example, methanol, ethanol, isopropyl alcohol or n-butanol or benzyl alcohol saturated with anhydrous HCl, then evaporating the solvent to afford the appropriate ester.

The tert-butyl ester of the compounds of Formula I are prepared by treating the free acid of Formula I in dioxane-$H_2SO_4$ (10:1) containing an excess of isobutylene at about 25° C. for about 2 to 24 hours.

The compounds of Formula XVII wherein X is pro, ala or leu and Y and Z form a single bond are either known in the art or are prepared by well known general procedures.

The compounds of Formula XVII wherein Y-X is ala-pro, ala-ala or ala-leu and Z forms a single bond are prepared by reacting equimolar amounts of a compound of the formula $R_{30}Y-OH$, wherein $R_{30}$ has the meaning defined in Formula XVI and Y is ala, with the tert-butyl ester of proline, alanine or leucine, in the presence of a suitable coupling reagent, for example, EEDQ, DCC or TMSN=C=N-TMS, followed by removal of the tert-butyl function by treatment with trifluoroacetic acid.

The compounds of Formula XVII wherein Z-Y-X is ala-ala-pro, ala-ala-ala or pro-ala-leu, are prepared by coupling equimolar amounts of the methyl ester of proline, alanine or leucine with tert-butoxycarbonylalanine using a coupling reagent such as EEDQ, DCC or TMSN=C=N-TMS to afford the methyl ester of tert-butoxycarbonylalanylproline, tert-butoxycarbonylalanylalanine or tert-butoxycarbonylalanylleucine, respectively. The tert-butoxycarbonyl function is removed by treatment with trifluoroacetic acid and 1 equivalent of the resultant amine product is then coupled with 1 equivalent of a compound of the formula $R_{30}Z-OH$, wherein $R_{30}$ has the meanings defined in Formula XVI and Z is ala or pro, using for example, one of the coupling reagents enumerated above. The methyl ester function is removed by treating the compound in an aqueous lower alcohol, such as methanol or ethanol, with alkali metal hydroxide, such as sodium, lithium and the like hydroxides, at about 25° C. for about 1 to 24 hours after which the reaction mixture is acidified and extracted with ether.

The compounds of Formula I are prepared by mixing, in the presence of 1 equivalent of suitable base, 1 equivalent of a bis ester of malonic acid of Formula II with 1 to 1.5 equivalents of an alkylating agent of Formula III to yield the triester of Formula IV:

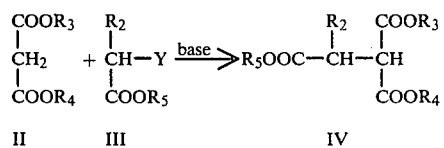

wherein the foregoing formulas Y is any good leaving group such as, for example, chloro, bromo, iodo, tosylate, mesylate and the like; $R_2$ is straight or branched alkyl having from 1 to 4 carbon atoms or benzyl; R₃ is tert-butyl, diphenylmethyl, triphenylmethyl or benzyl; R₅ is straight or branched alkyl having from 1 to 3 carbon atoms, 2,2,2-trichloroethyl or 2-(trimethylsilyl)ethyl; and R₄ is straight or branched alkyl having from 1 to 3 carbon atoms, tert-butyl, benzyl, diphenylmethyl, triphenylmethyl, 2,2,2-trichloroethyl or 2-(trimethylsilyl)ethyl.

Suitable bases for the reaction are alkali metal hydrides or alkoxides, such as, for example, sodium hydride, potassium hydride, sodium or potassium methoxide or ethoxide, potassium tert-butoxide and the like. The reaction mixture is stirred for about 24 hours at about 0° C. to about 100° C., preferably about 25° C., in a suitable solvent, such as a protic solvent, for example, a lower alkanol such as methanol, ethanol and the like or an aprotic solvent such as diethyl ether, tetrahydrofuran, hexane, benzene, dimethoxyethane, dioxane, acetamide, dimethylacetamide, dimethylsulfoxide, hexamethylphosphoramide and the like.

Typically, 1 equivalent of the malonate ester (II), from 1 to 1.5 equivalents of the alkylating agent (III) and 1 equivalent of sodium hydride are mixed in tetrahydrofuran at about 25° C. with stirring for about 6 hours.

One equivalent of the thus-obtained triester of Formula IV is treated with 1 equivalent of a suitable strong base, such as, for example, sodium hydride, potassium hydride, lithium hydride, lithium diisopropylamide, lithium carbide, lithium acetylide and the like, in an aprotic solvent, such as, for example, diethyl ether, tetrahydrofuran, hexane, benzene, dimethoxyethane, dioxane, dimethylacetamide, dimethyl sulfoxide, hexamethylphosphoramide and the like, for about 1 to 48 hours at a temperature of about 0° C. to 100° C., preferably about 25° C., after which an excess of an alkylating reagent of the formula: XR, wherein R is a fluorinated-methyl selected from CF₃, CHF₂ or CH₂F and X is chloro, bromo or iodo, is added to the reaction mixture with the additional requirement that, when said alkylating reagent is either XCF₃ or XCH₂F, then from 1 to 15 equivalents of hexamethylphosphoramide or dimethyl sulfoxide is added prior to alkylation. The reaction mixture is stirred from about 1 to 24 hours at about 25° C. to give the fluorinated-methyl triester of Formula V wherein R, R₂, R₃, R₄ and R₅ are as previously defined:

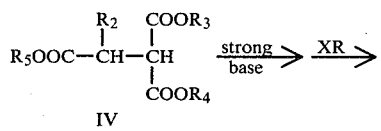

The fluorinated-methyl triester of Formula V is then de-esterified to the corresponding diester monoacid or monoester diacid of the formula:

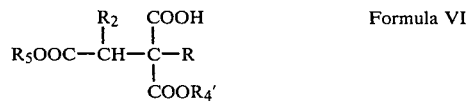

Formula VI wherein R'₄ is C₁-C₃ alkyl, benzyl, 2,2,2-trichloroethyl or 2-(trimethylsilyl)ethyl (thereby making COOR'₄ an ester function) or is hydrogen (thereby making COOR'₄ an acid function).

De-esterification of those compounds of Formula V, wherein R₃ is tert-butyl, diphenylmethyl or triphenylmethyl and R₅ is C₁₋₃ alkyl, 2,2,2-trichloroethyl or 2-(trimethylsilyl)ethyl, to the corresponding compounds of Formula VI is readily achieved by selective hydrolysis, for example, by treatment with trifluoroacetic acid alone or with other mild acids, such as hydrochloric or sulfuric acid in an organic solvent, for example, an ether such as dioxane, diethyl ether, tetrahydrofuran and the like, for about ½ to 12 hours at a temperature of from about −30° C. to about 25° C., preferably about 0° C. In such hydrolysis, when R₄ is C₁₋₃ alkyl, benzyl, 2,2,2-trichloroethyl or 2-(trimethylsilyl)ethyl in Formula V, the one ester function, COOR₃, is de-esterified to yield the corresponding diester monoacid of Formula VI; and when R₄ is tert-butyl, diphenylmethyl or triphenylmethyl in Formula V, the two ester functions, COOR₃ and COOR₄, are de-esterified to yield the corresponding monoester diacid of Formula VI, i.e., wherein R'₄ equals hydrogen.

De-esterification of those compounds of Formula V, wherein R₃ is benzyl and R₅ is C₁₋₃ alkyl, trichloroethyl or 2-(trimethylsilyl)ethyl to the corresponding compounds of Formula VI is readily achieved by catalytic hydrogenolysis using, for example, rhodium or palladium on charcoal, Raney nickel or platinum oxide, in an appropriate aprotic solvent such as, for example, ethyl acetate, dioxane, diethyl ether, tetrahydrofuran and the like in the presence of hydrogen gas. In such hydrogenolysis, when R₄ is C₁-C₃ alkyl, 2,2,2-trichloroethyl or 2-(trimethylsilyl)ethyl in Formula V, the one ester function, COOBz, is de-esterified to yield the corresponding diester monoacid of Formula VI; and when R₄ is also benzyl in Formula V, the two COOBz ester functions are de-esterified to yield the corresponding monoester diacid of Formula VI, i.e., wherein R'₄ equals hydrogen.

When R'₄ in the compounds of Formula VI is hydrogen, said compounds are decarboxylated by treatment at 25° C. to 140° C. for about 1 to 24 hours in an acidic solvent selected from, for example, acetic acid, propionic acid, trifluoroacetic acid or mixtures thereof to give the corresponding monoester monoacid of the formula

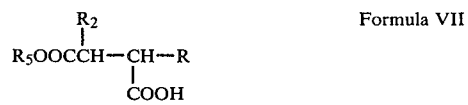

Formula VII wherein R, R₂ and R₅ are as previously defined, which is converted to the corresponding acid halide, e.g., acid chloride by, for example, treatment with excess thionyl chloride or with 1 to 3 equivalents of oxalyl chloride to 1 equivalent of the acid VII, preferably in the form of an alkali metal salt, e.g., the sodium or potassium salt, in a hydrocarbon solvent, such as an aromatic hydrocarbon, e.g., benzene, toluene and the like, at about −30° C. to 130° C. for about 1 to 24 hours. Said acid halides may also be obtained according to the methodology described in Ghosez et al., *Chem. Comm.*, p. 1180 (1979). The resultant acid halide is treated with the anion of the formula

Formula VIII wherein $R_6$ is a straight or branched alkyl having from 1 to 4 carbon atoms, phenyl or benzyl; Q is carbon or $CR_7R_8$, wherein $R_7$ is hydrogen, phenyl, straight or branched alkyl having from 1 to 8 carbon atoms and $R_8$ is equal to $R_7$ other than hydrogen, or $R_7$ and $R_8$ taken together form an alkylene group of from 4 to 6 carbon atoms, that is, $-CH_2-(CH_2)_m-CH_2-$ wherein m is an integer of from 2 to 4, the terminal bonds of such alkylene group attached to the N-linked carbon atom in formula VIII; and $R_1$ is a straight or branched alkyl having from 1 to 4 carbon atoms. The anion VIII is formed by the reaction of a Schiff base or an isonitrile with a base such as sodium hydride or an alkyllithium or a dialkylamide of lithium or potassium. One equivalent of the anion of Formula VIII is added to 1 equivalent of the acid halide in an aprotic solvent, for example, benzene, diethyl ether, dioxane, tetrahydrofuran, dimethyl sulfoxide, hexamethylphosphoramide and the like. The reaction is carried out at temperatures of about $-120°$ C. to 25° C., preferably about $-78°$ C. for about ½ to 24 hours.

The resulting Schiff base adduct of Formula IX, wherein R, $R_1$, $R_2$, $R_5$, $R_6$ and Q are as previously defined, is then hydrolyzed to the product of Formula I:

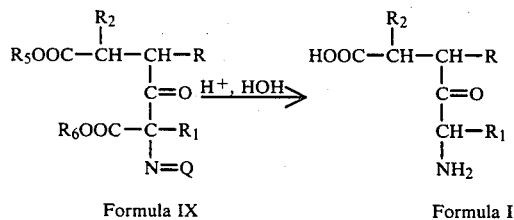

Formula IX      Formula I

The transformation of IX to I is achieved under acidic hydrolysis conditions, for example, by treatment of IX with a strong acid (1 M to 6 M) such as, for example, hydrochloric acid, hydrobromic acid, trifluoroacetic acid, sulfuric acid and the like, at from about 5° C. to about 100° C., with or without a cosolvent such as, for example, acetic acid, dioxane, etc., for about ½ hour to 4 days. Decarboxylation of the $-COOR_6$ group occurs during the hydrolysis as well as conversion of the $-N=Q$ function to $-NH_2$.

Alternatively, when $R_5$ and $R_6$ are benzyl, the $N=Q$ function may be converted to an $NH_2$ function by mild acid hydrolysis using, for example, 1 N hydrochloric, trifluoroacetic or sulfuric acids at about 25° C. for about ½ hour to 4 hours. The resultant amine derivative is debenzylated by hydrogenolysis, or treated with iodotrimethylsilane neat at a temperature of about 25° C. to about 100° C. for about 1 to about 48 hours or, optionally, the latter may be carried out in a solvent such as acetonitrile, carbon tetrachloride, chloroform, dichloromethane and the like, at the reflux temperature of the solvent in order to remove the 2 benzyl ester groups with decarboxylation of the $-COOR_6$ group occurring spontaneously. If either of $R_5$ or $R_6$ is other than benzyl, the ester functions may be finally hydrolyzed using stronger acid conditions as generally described hereinabove.

Furthermore, when R is $CHF_2$ in Formula VII, 1 equivalent of such compound may be treated with 2 equivalents of a base, such as, sodium or potassium hydroxide, pyridine or a trialkylamine such as triethylamine in water or mixtures of water and a lower alcohol, such as methanol or ethanol, or tetrahydrofuran or dioxane to give the unsaturated acid of Formula X, which is hydrogenated catalytically using, for example, rhodium or palladium on charcoal or Raney nickel or platinum oxide catalysts. The reaction time varies from about 1 to about 24 hours at a temperature of about 25° C. to 100° C. with a pressure variation of about 1 to 12 atmospheres to give the compound of Formula VII wherein R is $CH_2F$.

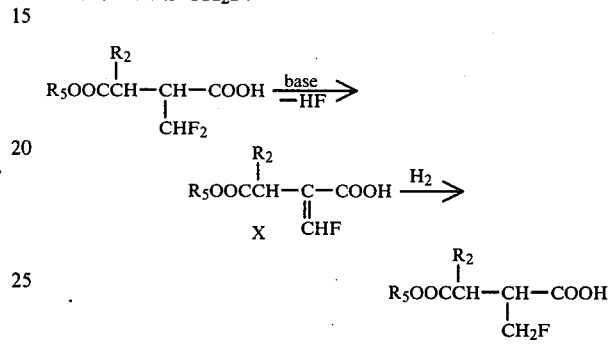

When in the compounds of Formula VI the group $R'_4$ is other than hydrogen, said compounds are converted to the corresponding acid halide, e.g., chloride, by the procedures generally described hereinabove followed by treatment with a Schiff base anion of Formula VIII under the general reaction conditions described hereinabove followed by acid hydrolysis using, e.g., 1 M to 6 M hydrochloric, hydrobromic, trifluoroacetic or sulfuric acids with or without the addition of cosolvents, such as acetic acid or dioxane, said hydrolysis being carried out at temperatures of about 5° C. to 100° C. for about 1 to 4 days to afford compounds of Formula I.

Another method for preparing the compounds of Formula I utilizes a nitrile of either Formula XI-a or XI-b:

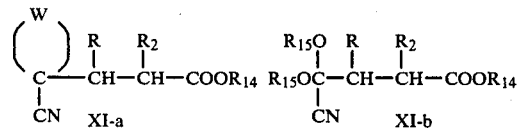

wherein

is 2-cyano-1,3-dithian-2-yl; R and $R_2$ have the respective meanings defined in Formula I; and $R_{14}$ and $R_{15}$ are each a straight or branched $C_{1-4}$ lower alkyl. The ester function, $COOR_{14}$, is hydrolyzed with appropriate base, i.e., suitable for ester-to-acid alkaline hydrolysis reactions, for example, by treatment with an alkali metal hydroxide in an aqueous lower alkanol such as, for example, potassium hydroxide in ethanol or methanol at about 25° C. to 100° C. for about 1 to about 10 hours, to give the corresponding free acid which is in turn treated with an appropriate lithium or Grignard reagent of the respective formulas, $R_1Li$ or $R_1Mg$-halo, wherein $R_1$ is straight or branched $C_{1-4}$ lower alkyl and halo is bromo, fluoro or iodo, to give the corresponding imines of Formulas XII-a or XII-b, respectively:

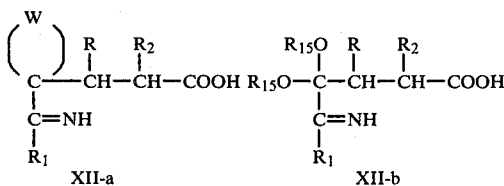
XII-a  XII-b which can be (i) reduced in situ to the corresponding amine utilizing sodium or lithium cyanoborohydride as the reducing agent, or (ii) hydrolyzed to the corresponding ketone which in turn is subjected to reductive amination with sodium or lithium cyanoborohydride, to give the corresponding amines of Formulas XIII-a or XIII-b, respectively:

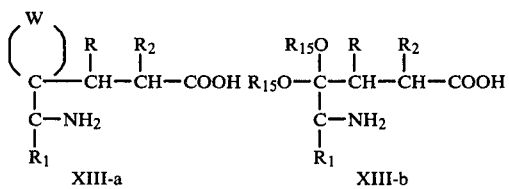
XIII-a  XIII-b followed by thioketal hydrolysis of the Formula XIII-a compounds or acid hydrolysis of the Formula XIII-b compounds to give the desired compounds of Formula I.

Treatment of the free acids of the compounds of Formulas XI (a and b) with an appropriate lithium or Grignard reagent of the formulas $R_1Li$ or $R_1Mg$-halo as described above is carried out by reacting 1 equivalent of the free acid and 2 equivalents of the lithium or Grignard reagent in an ether solvent such as, for example, diethyl ether, 1,2-dimethoxyethane, dioxane, tetrahydrofuran and the like, for about 1 minute to 3 hours at a temperature of about −78° C. to 0° C.

Imine reduction as described hereinabove is achieved by treatment with sodium or lithium cyanoborohydride of the Grignard product which has been quenched by ethanolic ammonium acetate at about 0° C. to 25° C. for about 1 to 48 hours.

Reductive amination noted hereinabove involves acid hydrolysis of the Grignard product to afford the corresponding ketone which is then subjected to treatment with sodium or lithium cyanoborohydride in the presence of alcoholic ammonium acetate.

Thioketal hydrolysis as described hereinabove is achieved by treatment with excess methyl iodide, mercuric chloride or N-bromosuccinimide in aqueous acetonitrile, dimethylformamide or acetone for about 1 to 24 hours at about 25° C. to 60° C. in the presence of 1 equivalent of acid such as, for example, hydrochloric acid, acetic acid and the like.

In addition, the compounds of Formula I may be obtained by reacting equimolar amounts of an aldehyde of Formula XIV, wherein R, $R_2$ and $R_{14}$ are as previously described, and in particular, wherein $R_{14}$ is tert-butyl, and a lithium or Grignard reagent of the respective formulas, $R_1Li$ or $R_1Mg$-halo, wherein $R_1$ and halo are as previously described, in an ether solvent, such as, for example, diethyl ether, 1,2-dimethoxyethane, dioxane, tetrahydrofuran and the like, for about 1 minute to 3 hours at a temperature of about −78° C. to about 0° C. to give the corresponding alcohol of Formula XV:

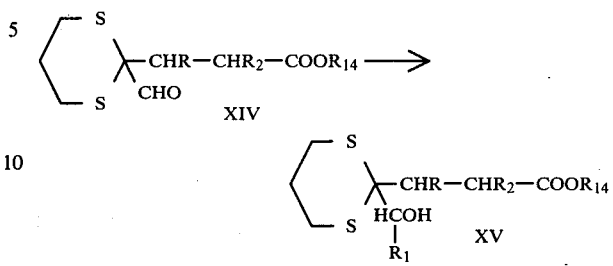

which is in turn treated with triphenylphosphine, phthalimide and diethyl azodicarboxylate in tetrahydrofuran at about 25° C. to 60° C. for about 1 to 24 hours to give the corresponding substituted phthalimide. The phthalimide is converted to the corresponding lactam (when $R_{14}$ is straight alkyl) or amine (when $R_{14}$ is branched alkyl, e.g., tertbutyl) by treatment with hydrazine or N,N-dimethylpropane-1,3-diamine followed by thioketal hydrolysis and lactam hydrolysis or tert-butyl ester hydrolysis, respectively, to give the appropriate compound of Formula I.

The compounds of Formulas XI-a, XI-b and XIV are prepared by adding 1 equivalent of 1,3-dithiane-2-carbonitrile or 1 equivalent of di-(lower alkoxy)acetonitrile or 1 equivalent of 1,3-dithiane-2-carboxaldehyde, respectively, (the latter being optionally converted to the N,N-dimethylhydrazone) to 1 equivalent of a base, such as lithium diisopropylamide, sodium or potassium hydride, an alkyl lithium, such as methyl lithium or n-butyllithium or lithium tetramethylpiperidide in an ether solvent, such as, for example, tetrahydrofuran, dioxane, diethyl ether and the like, optionally in the presence of hexamethylphosphoramide at a temperature of about −70° C. to 0° C., preferably −78° C. and after about 1 to 30 minutes 1 equivalent of fluorinated-methyl substituted acrylate of the formula

wherein R has the meaning defined in Formula I, and $R_{14}$ is a straight or branched $C_{1-4}$ lower alkyl. The reaction is permitted to proceed for about 1 to 30 minutes at about −70° C. to 0° C. after which 1 equivalent of an alkylating reagent of the formula $R_2Y$ is added to the reaction mixture and the alkylation permitted to proceed at a temperature of about −70° C. to 0° C. for about 1 to 12 hours with the additional step of treatment with dilute acid (28° C. for 24 hours, ether two-phase system) when the N,N-dimethylhydrazone is employed. $R_2$ has the meaning defined in Formula XIV and Y is any good leaving group, such as halogen, for example, chlorine, bromine or iodine, or mesyl or tosyl.

Still further, the subject compounds of Formula I may be prepared by the procedure outlined in copending U.S. patent application Ser. No. 160,057, filed on the same date as the instant application by Jerry L. Adams and the co-inventor of the instant application, Brian W.

Metcalf, and entitled Production of Intermediates for Enzyme Inhibitors.

The following Examples are presented for purposes of illustrating, but not of limiting, the invention described herein. Unless otherwise indicated, all parts are by weight.

EXAMPLE 1

3-Alanyl-4,4,4-trifluoro-2-methylbutyric acid

The above named compound is prepared by treating 317 mg (1 mMole) of 3-[2-(1-aminoethyl)1,3-dithian-2-yl]-4,4,4-trifluoro-2-methylbutyric acid with 1.0 ml of 1 N HCl and 10 ml of acetonitrile followed by treatment with 2 ml of methyl iodide. The mixture is stirred at 25° C. for 48 hours then diluted with water. The mixture is then thoroughly washed with ether and the aqueous phase is concentrated to afford 3-alanyl-4,4,4-trifluoro-2-methylbutyric acid.

Alternatively, 800 mg of N-bromosuccinimide can be used in place of methyl iodide.

EXAMPLE 2

3-(2-Formyl-1,3-dithian-2-yl)-4,4,4-trifluoro-2-methylbutyric acid ethyl ester

A solution of 1.47 g (10 mMole) of 1,3-dithiane-2-carboxaldehyde in 10 ml of tetrahydrofuran is added to lithium diisopropylamide, prepared from diisopropylamine (1.01 g, 10 mMole) and butyllithium (4.8 ml of a 2.1 M solution, 10 mM) in 20 ml of tetrahydrofuran at −70° C. To the solution is added 1.60 g (9.5 mMole) of 3-trifluoromethylacrylic acid ethyl ester in 5 ml of tetrahydrofuran and the reaction mixture is stirred at −70° C. for 30 minutes after which 1.3 g (10 mMole) of methyl iodide is added and the mixture is maintained at 0° C. for 15 hours then poured into aqueous ammonium chloride and extracted with ether. The ether solution is dried and evaporated to give the title compound.

When in the above procedure 1.6 g (10 mMole) of benzyl bromide is used in place of methyl iodide, 3-(2-formyl-1,3-dithian-2-yl)-4,4,4-trifluoro-2-benzylbutyric acid ethyl ester is obtained.

EXAMPLE 3

3-(2-Formyl-1,3-dithian-2-yl)-4,4,4-trifluoro-2-methyl butyric acid.

A solution of 3 g of the ethyl ester of Example 2, paragraph 1, in 40 ml of ethanol is treated with 25% aqueous sodium hydroxide for about 15 hours at 25° C. The mixture is then acidified and extracted well with chloroform. The organic phase is dried and concentrated to afford the title compound.

EXAMPLE 4

3-[2-(1-Hydroxyethyl)-1,3-dithian-2-yl]-4,4,4-trifluoro-2-methylbutyric acid methyl ester A solution of 864 mg (3 mMole) of the product of Example 3 in 15 ml of tetrahydrofuran is treated dropwise with methylmagnesium iodide (6 ml of a 1 M solution). After 1 hour at −78° C. the mixture is quenched with 1 N HCl and extracted with ether. The ether solution is dried and evaporated. The residue is treated with excess diazomethane in ether then evaporated to give the title compound.

EXAMPLE 5

A solution of 462 mg (2 mMole) of the product of Example 4 in 20 ml of tetrahydrofuran is treated with 524 mg (2 mMole) of triphenylphosphine, 268 mg (2 mMole) of phthalimide, and 350 mg (2 mMole) of diethyl azodicarboxylate for 48 hours at 25° C. The solvent is evaporated and the product isolated by chromatography on silica gel affording 3-[2-(1-phthalimidoethyl)-1,3-dithian-2-yl]-4,4,4-trifluoro-2-methylbutyric acid methyl ester.

EXAMPLE 6

3-[2-(1-aminoethyl)-1,3-dithian-2-yl]-4,4,4-trifluoro-2-methylbutyric acid hydrochloride A solution of 1.1 g of the product of Example 5 in 20 ml of ethanol is treated with hydrazine hydrate (2 ml) for 2 hours at reflux. The ethanol is evaporated and the residue treated with 1 N NaOH then extracted with ether. The ether solution is dried and concentrated leaving a residue that is taken up in 20 ml of ethanol and 10 ml of 6 N HCl and heated at reflux for 1 hour. The solvents are evaporated to give the title compound.

EXAMPLE 7

2-Methyl-4,4,4-trifluoro-3-(N-acetylalanylprolylalanyl)butyric acid methyl ester.

A solution of 500 mg of 3-(alanyl)-4,4,4-trifluoro-2-methylbutyric acid in 50 ml of methanol is saturated with anhydrous HCl at 0° C. then allowed to stand at 25° C. for 15 hours. The solvent is evaporated to afford the hydrochloride of corresponding methyl ester.

Triethylamine (100 mg, 1 mMole) is added to a mixture of 228 mg (1 mMole) of N-acetylalanylproline (Thompson and Blout, Biochem. 12, 58, (1973)), 280 mg (1 mMole) of the above obtained methyl ester hydrochloride, 250 mg (1 mMole) of EEDQ in 15 ml of dichloromethane at 25° C. The mixture is stirred for 12 hours at 25° C., then is diluted with 100 ml of ether and washed with 1 N HCl, aqueous sodium bicarbonate and brine, then dried and evaporated to afford the title product.

EXAMPLE 8

3-(N-acetylalanylalanylprolylalanyl)-4,4,4-trifluoro-2-methylbutyric acid

Isobutylene (15 g) is added to mixture of 3-(alanyl)-4,4,4-trifluoro-2-methylbutyric acid (1 g) in dioxane (15 ml) and concentrated sulfuric acid (1.5 ml) in a 500 ml pressure bottle. The mixture is shaken mechancially at 25° C. for 6 hours then poured into ether and washed with aqueous bicarbonate. The organic phase is dried and concentrated to afford the corresponding tertbutyl ester.

Triethylamine (100 mg, 1 mMole) is added to a mixture of N-acetylalanylalanylproline (300 mg, 1 mMole), the tert-butyl ester obtained above (290 mg, 1 mMole) and EEDQ (247 mg) in dichloromethane (15 ml). The mixture is stirred for 15 hours at 25° C., then diluted with ether, washed with 1 N HCl, aqueous bicarbonate, dried and evaporated. The residue is treated at 0° C. with 2 ml of trifluoroacetic acid for 10 minutes then the TFA is evaporated under reduced pressure to afford the title compound.

EXAMPLE 9

N,N-Diethyl-3-(N-acetylalanylalanylprolylalanyl)-4,4,4-trifluoro-2-methylbutyramide To 440 mg (1 mMole) of the product of Example 8 in 10 ml of acetonitrile at −20° C. is added 150 mg (2.1 mMole) of diethylamine and 140 mg (1 mMole) of isobutyl chloroformate. The reaction mixture is allowed to warm to 25° C. and stirred 15 hours at 25° C. The mixture is then diluted with ethyl acetate and washed with 1 N HCl, aqueous bicarbonate, then dried and evaporated to give the title compound.

EXAMPLE 10

N-Acetylalanylalanylproline

EEDQ (250 mg, 1 mMole) is added to a mixture of 190 mg (1 mMole) of tert-butoxycarbonylalanine and 130 mg (1 mMole) of methyl prolinate in 20 ml of dichloromethane. After 12 hours at 25° C., the solution is diluted with ether and washed with 1 N HCl, aqueous bicarbonate, dried and evaporated. The residue is treated with 2 ml of trifluoroacetic acid at 0° C. for 5 minutes then the solvent is evaporated under reduced pressure to afford the amine trifluoroacetate salt which is treated in 15 ml of dichloromethane with 101 mg (1 mMole) of triethylamine, 130 mg (1 mMole) of N-acetylalanine, and 247 mg (1 mMole) of EEDQ for 12 hours at 25° C. The mixture is then diluted with ether, washed with 1 N HCl, aqueous bicarbonate, dried and evaporated. The residue is taken up in 10 ml of methanol containing 25 mg of lithium hydroxide and stirred at 25° C. for 15 hours. The methanol is removed under reduced pressure and the residue acidified with 0.5 N HCl and extracted with ethyl acetate. The organic phase is dried and concentrated to give the title compound.

EXAMPLE 11

1-t-Butyl 6-methyl 2-benzylideneamino-4-difluoromethyl-2,5-dimethyl-3-oxohexanedioate A solution of t-butyl 2-(benzylideneamino)propionate (0.1 mMole, 23.3 g) in 50 ml of anhydrous THF is added at room temperature and under nitrogen to a suspension of sodium hydride (0.11 mMole), prewashed with pentane, in 100 ml of anhydrous THF. After stirring for 16 hours, the homogeneous solution is cooled to −70° C. and a solution of methyl 3-chloroformyl-4,4-difluoro-2-methyl butanoate (0.1 mMole) in 100 ml of anhydrous THF is added dropwise over a period of 2 hours. Stirring is continued for 1 hour and the mixture is hydrolyzed at −70° C., saturated with NaCl and extracted with ethyl acetate. The organic phase is washed with brine, dried over magnesium sulfate and concentrated in vacuo. The desired diester compound is isolated by chromatography on silica gel using a gradient of ethyl acetate toluene as eluant.

1-t-Butyl 6-methyl 2-benzylideneamino-4-benzyloxycarbonyl-4-difluoro-methyl-2,5-dimethyl-3-oxohexanedioate, is prepared in a similar manner except that methyl 3-benzyloxycarbonyl-3-chloroformyl-4,4-difluoro-2-methylbutanoate, is used respectively in place of methyl 3-chloroformyl-4,4-difluoro-2-methyl butanoate.

1-t-Butyl 6-methyl 2-benzylideneamino-2-benzyl-4-difluoromethyl-5-methyl-3-oxohexanedioate is prepared in a similar manner except that t-butyl 3-phenyl-2-benzylideneamino propionate is used in place of t-butyl 2-benzylideneaminopropionate.

1-t-butyl 6-methyl 2-benzylideneamino-2-benzyl-4-benzyloxycarbonyl-4-difluoromethyl-5-methyl-3-oxohexanedioate is prepared in a similar manner except that t-butyl 3-phenyl-2-benzylideneaminopropionate is used in place of t-butyl 2-benzylideneaminopropionate and methyl 2-benzyl-3-benzyloxycarbonyl-3-chloroformyl-4,4-difluorobutanoate and methyl 3-benzyloxycarbonyl-3-chloroformyl-4,4-difluoro-2-methyl butanoate are used respectively in place of methyl 3-chloroformyl-4,4-difluoro-2-methylbutanoate.

EXAMPLE 12

1-tert-Butyl 4-methyl 2-tert-butoxycarbonyl-3-benzylbutanedioate

Di-tert-butyl malonate (100 mMole, 21.6 g) is added, at room temperature and under nitrogen, to a suspension of sodium hydride (110 mMole, 4.950 g of a 55% dispersion in oil) in tetrahydrofuran (280 ml). After stirring for 1 hour, a solution of methyl 2-bromo-3-phenylpropionate (100 mMole) in tetrahydrofuran (20 ml) is added dropwise over a period of 15 minutes. Stirring is continued for 48 hours at room temperature. The mixture is then hydrolyzed and extracted twice with diethyl ether. The organic layer is dried over anhydrous magnesium sulfate and concentrated to dryness in vacuo. The desired triester compound is isolated by distillation under reduced pressure: b.p. 120° C./0.1 mm Hg.

Similarly, 1-t-butyl 4-methyl 2-t-butoxycarbonyl-3-methyl butanedioate is obtained from methyl 2-bromopropionate.

1-t-Butyl 4-(2,2,2-trichloroethyl) 2-benzyloxycarbonyl-3-benzyl butanedioate; 1-t-butyl 4-(2,2,2-trichloroethyl) 2-benzyloxycarbonyl-3-methyl butanedioate are prepared from t-butyl benzyl malonate and the corresponding bromotrichloroester.

EXAMPLE 13

2-Difluoromethyl-2-tert-butoxycarbonyl-3-methylbutanedioic acid, 1-tert-butyl, 4-methyl ester 2-tert-Butoxycarbonyl-3-methylbutanedioic acid, 1-tert-butyl, 4-methyl ester (40 mMole, 11.520 g) prepared in Example 12 is added, at room temperature and under nitrogen, to a suspension of sodium hydride (120 mMole, 5.400 g of a 55% dispersion in oil) in tetrahydrofuran (200 ml). After stirring for 1 hour, a stream of chlorodifluoromethane is rapidly bubbled through the anion solution. Stirring is continued for 20 hours and the mixture is quenched with water and extracted twice with diethyl ether. The organic layer is dried over anhydrous magnesium sulfate, and concentrated to dryness in vacuo. The residual oil is crystallized from diethyl ether/petroleum ether mixture to yield the desired difluoromethylated triester: m.p. 49° C. to 50° C., yield 12.100 g (about 90%).

EXAMPLE 14

2-Difluoromethyl-3-methylbutanedioic acid, 4-methyl ester

2-Difluoromethyl-2-(tert-butoxycarbonyl)-3-methylbutanedioic acid, 1-(tert-butyl)4-methyl ester (6.5 mMole, 2.210 g) prepared in Example 13 is dissolved in trifluoroacetic acid (10 ml) at room temperature. After stirring for 1.5 hours at room temperature, the solvent is evaporated in vacuo yielding the desired acid. Treatment of this acid with excess thionyl chloride gives the acid chloride.

EXAMPLE 15

5-Amino-3-difluoromethyl-2-methyl-4-oxohexanoic acid hydrochloride

A solution of methyl 5-amino-3-difluoromethyl-2-methyl-4-oxohexanoate in aqueous HCl 4 M is stirred at room temperature for 12 hours. Concentration in vacuo affords the desired substituted δ-amino levulinic acid derivative.

EXAMPLE 16

Methyl 5-amino-3-difluoromethyl-2-methyl-4-oxohexanoate hydrochloride

A mixture of 1-t-butyl 6-methyl 2-benzylideneamino-4-difluoromethyl-2,5-dimethyl-3-oxohexanedioate (0.5 mMole), methanol (50 ml) and 1 M aqueous hydrochloric acid (150 ml) is stirred at room temperature for 12 hours. Concentration of the solvent in vacuo leaves a residue which is washed several times with pentane. The residual solid is dissolved in methanol. Addition of a mixture of ether and pentane precipitates the desired title compound.

Methyl 5-amino-2-benzyl-3-difluoromethyl-4-oxohexanoate hydrochloride is prepared in a similar manner except that 1-t-butyl 6-methyl 2-benzylideneamino-5-benzyl-4-difluoromethyl-2-methyl-3-oxohexanedioate is used in place of 1-t-butyl 6-methyl 2-benzylideneamino-4-difluoromethyl-2,5-dimethyl-3-oxohexanedioate.

EXAMPLE 17

A mixture of 1-t-butyl 6-methyl 2-benzylideneamino 4-benzyloxycarbonyl-4-difluoromethyl-2,5-dimethyl-3-oxohexanedioate (0.1 mole) in 100 ml of methanol and 150 ml 1 M aqueous HCl is stirred at room temperature for 12 hours. Concentration of the solvent in vacuo leaves a residue which is washed several times with pentane. The residue is dissolved in 150 ml of methanol and 3 g of Pd/C 5% and 1 ml of concentrated HCl are added. The mixture is stirred under an atmosphere of H$_2$ for 12 hours. Concentration of the solvent in vacuo leaves the desired δ-amino levulinate hydrochloride derivative.

Similarly the other methyl and benzyl substituted δ-amino levulinate hydrochloride are prepared from the corresponding Schiff base triester compound.

EXAMPLE 18

4,4-Difluoro-2,3,3-butanetricarboxylic acid, 3-phenylmethyl 2-(2,2,2-trichloroethyl) ester

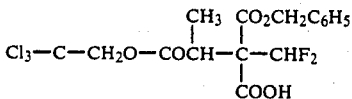

4,4-Difluoro-2,3,3-butanetricarboxylic acid, 3-t-butyl-3-phenyl-methyl 2-(2,2,2-trichloromethyl) ester (11 mMole), 5.63 g) is dissolved in trifluoroacetic acid (18 ml) at room temperature. After stirring for 2 hours, at room temperature, the solvent is evaporated in vacuo yielding an oil.

NMR (CDCl$_3$) 1.46 and 1.53 ppm (two d, J$_{HH}$=7 Hz, 3H) 3.53 ppm (m, 1H) 4.63 ppm (m, 2H) 5.20 ppm (s,2H) 6.35 ppm (t, J$_{HF}$=53 Hz, 1H) 7.25 ppm (s, 5H) 1.41 ppm (s,1H).

EXAMPLE 19

2-Chlorocarbonyl-2-difluoromethyl-3-methyl butanedioic acid, 1 phenylmethyl 4-(2,2,2-trichloroethyl) ester

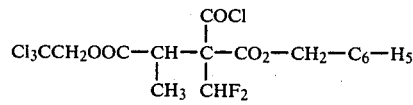

The crude 4,4-difluoro-2,3,3-butanetricarboxylic acid, 3-phenylmethyl 2-(2,2,2-trichloroethyl) ester is dissolved in thionyl chloride (40 ml), one drop of dimethyl formamide is added and the mixture is refluxed during 2 hours. Removal of the solvent in vacuo afforded the expected acid chloride as an oil.

NMR (CDCl$_3$) 1.46 and 1.6 ppm (two d, J$_{HH}$=7 Hz, 3H) 3.73 ppm (m, 1H) 4.61 ppm (m, 2H) 5.18 ppm (s, 2H) 6.45 ppm (t, J$_{HF}$=53 HZ, 1H) 7.21 ppm (s, 5H).

EXAMPLE 20

1,1,2-Propanetricarboxylic acid, 1-(1,1-dimethylethyl) 1-phenyl methyl 2-(2,2,2-trichloroethyl) ester

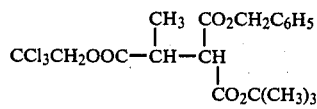

(1-Tert-butyl) 3-phenylmethyl malonate (35 mMole, 8.75 g) in tetrahydrofuran (45 ml) is added dropwise, at room temperature, under nitrogen, to a suspension of sodium hydride (35 mMole, 1,53 g of 55% dispersion in mineral oil) in tetrahydrofuran (60 ml). After stirring for 2 hours, a solution of 2-bromopropanoic acid, 2,2,2-trichloroethyl ester (35 mMole, 9.95 g) in tetrahydrofuran (40 ml) is added dropwise; stirring is continued overnight. The mixture is then hydrolized with a saturated aqueous solution of ammonium chloride and then tetrahydrofuran is evaporated in vacuo. The mixture is dissolved in ether and washed with water, the aqueous layer is extracted back twice with ether. The organic layer is washed with brine, dried over magnesium sulfate and concentrated in vacuo to afford an oil which gives after flash chromatography on silica gel with a 97/3 mixture (v/v) of toluene ethylacetate about 9.57 g of the expected triester (yield 62%).

NMR (CDCl) 1.23 and 1.3 ppm (two d J$_{HH}$=7 Hz, 3H) 1.33 ppm (s, 9H) 3.3 ppm (m, 1H) 3.7 ppm (m, 1H) 4.63 ppm (m, 2H) 5.1 ppm (s, 2H) 7.23 ppm (s, 5H).

EXAMPLE 21

4,4-Difluoro-2,3,3-butanetricarboxylic acid, 3-(1,1-dimethylethyl) 3-phenylmethyl, 2-(2,2,2-trichloroethyl) ester

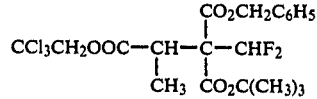

1,1,2-Propanetricarboxylic acid, 1-(1,1-dimethylethyl)-1-phenylmethyl-2-(2,2,2-trichloroethyl) ester (21 mMole, 9.57 g) in tetrahydrofuran (40 ml) is added dropwise, at room temperature, to a suspension of sodium hydride (23.1 mMole, 1.01 g of a 55% dispersion in mineral oil) in tetrahydrofuran (300 ml). After stirring for 3 hours, a stream of chlorodifluoromethane is bubbled through the anion solution. Stirring is continued under an atmosphere of chlorodifluoromethane overnight. The mixture is then hydrolyzed with a saturated aqueous solution of ammonium chloride and then tetrahydrofuran is evaporated in vacuo. The mixture is dissolved in ether and washed with water; the aqueous layer is extracted back twice with ether. The organic layer is washed with brine, dried over magnesium sulfate and concentrated in vacuo to afford an oil which gives after flash chromatography on silica gel with a 65/35 mixture of methylene chloride-petroleum ether 6.2 g of the expected triester (yield 59%) as an oil which was crystallized from pentane (only one isomer crystallized). m.p.=70°-71° C.

| Analysis calculated $C_{20}H_{23}Cl_3F_2O_6$ | |
| --- | --- |
| C 47.69 | C 47.66 |
| H 4.60 | H 4.58 |

NMR (CDCl$_3$) of the crystallized product 1.36 ppm (s, 9H) 1.46 and 1.50 (two d, $J_{HH}$=7 Hz, 3H) 3.63 ppm (q, $J_{HH}$=7 Hz, 1H) 4.65 ppm (A.Bq, $J_{AB}$=14 Hz, 2H) 5.18 ppm (s, 2H) 6.41 ppm (t, $J_{HF}$=54 Hz, 1H) 7.26 ppm (s, 5H).

EXAMPLE 22

3-(2-Cyano-1,3-dithian-2-yl)-4-fluoro-2-methylbutyric acid ethyl ester

A solution of 1.45 g (10 mMole) of 1,3-dithian-2-carbonitrile in 10 ml of tetrahydrofuran is added to lithium diisopropylamide, prepared from diisopropylamine (1.01 g, 10 mMole) and butyllithium (4.8 ml of a 2.1 M solution, 10 mM) in 20 ml of tetrahydrofuran at −70° C. To the solution is added 1.25 g (9,5 mMole) of 3-monofluoromethylacrylic acid ethyl ester in 5 ml of tetrahydrofuran and the reaction mixture is stirred at −70° C. for 30 minutes after which 1.3 g (10 mMole) of methyl iodide is added and the mixture is maintained at 0° C. for 15 hours, then poured into aqueous ammonium chloride and extracted with ether. The ether solution is dried and evaporated to give the title compound.

When in the above procedure 1.6 g (10 mMole) of benzyl bromide is used in place of methyl iodide, 3-(2-cyano-1,3-dithian-2-yl)-4-fluoro-2-benzylbutyric acid ethyl ester is obtained.

EXAMPLE 23

3-(2-Cyano-1,3-dithian-2-yl)-4-fluoro-2-methylbutyric acid

A solution of 3 g of the ethyl ester of Example 22, paragraph 1, in 40 ml of ethanol is treated with 15 ml of a 1 M solution of lithium hydroxide for about 40 hours at 25° C. The mixture is then acidified and extracted well with chloroform. The organic phase is dried and concentrated to afford the title compound.

EXAMPLE 24

3-[2-(1-Aminoethyl)-1,3-dithian-2-yl]-4-fluoro-2-methylbutyric acid methyl ester A solution of 4-cyano-4-(1,3-dithian-2-yl)-3-monofluoromethyl-2-methylbutyric acid (819 mg, 3mMole) in THF (15 ml) at −70° C. is treated dropwise with methyl lithium (6 ml of a 1 M solution). After 1 hour at −70° C., the mixture is quenched with acetic acid (360 mg, 6 mMole). On warming to room temperature ammonium acetate (2.8 g, 33 mMole) is added followed by lithium cyanoborohydride (110 mg, 2.1 mMole) in methanol (15 ml). The mixture is stirred for 48 hours at 25° C., then concentrated HCl is added until pH 2, then the mixture is concentrated to dryness. The residue is then treated for 16 hours at 25° C. with a solution of methanol saturated with anhydrous HCl. The solvent is evaporated, the residue basified with aqueous potassium carbonate and extracted with ether. Evaporation of the organic phase affords the title compound.

We claim:

1. A compound of the formula

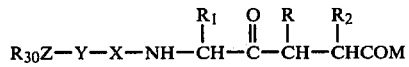

wherein R is CF$_3$, CHF$_2$ or CH$_2$F; R$_1$ is a straight or branched lower alkyl group having from 1 to 4 carbon atoms; R$_2$ is defined the same as R$_1$ or is benzyl; R$_{30}$ is CHO, carbobenzoxy, tert-butoxycarbonyl, benzoyl or a lower alkanoyl group having from 2 to 5 carbon atoms; X is pro, ala or leu and Y and Z together form a single bond; or Y-X is ala-pro, ala-ala or ala-leu and Z is a single bond; or Z-Y-X is ala-ala-pro, ala-ala-ala or pro-ala-leu; and M is hydroxy, a straight or branched lower alkoxy group having from 1 to 4 carbon atoms, benzyloxy or NY$_1$Y$_2$ wherein each of Y$_1$ and Y$_2$ is hydrogen or a lower alkyl group having from 1 to 4 carbon atoms and can be the same or different; and pharmaceutically acceptable salts thereof.

2. A compound of claim 1 wherein M is hydroxy or a lower alkoxy group.

3. A compound of claim 1 wherein R is CHF$_2$.

4. A compound of claim 1 wherein R$_1$ is methyl.

5. A compound of claims 3 or 4 wherein R$_{30}$ is acetyl.

6. A compound of claim 1 which is 3-(N-acetylalanyl-prolylalanyl)-4,4-difluoro-2-methylbutyric acid.

* * * * *